United States Patent [19]
Sanker et al.

[11] Patent Number: 5,980,869
[45] Date of Patent: *Nov. 9, 1999

[54] DUAL PHASE ORAL COMPOSITIONS COMPRISING A PLANT EXTRACT FROM THE ERICACEAE FAMILY

[75] Inventors: Lowell Alan Sanker; Stephen James Nilsen, both of Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/848,627

[22] Filed: Apr. 28, 1997

[51] Int. Cl.$^6$ .............................. A61K 7/26; A61K 7/16; A61K 7/18
[52] U.S. Cl. .............................. 424/58; 424/49; 424/52; 424/56; 424/57
[58] Field of Search ........................................ 424/49–58

[56] References Cited

U.S. PATENT DOCUMENTS

| | | |
|---|---|---|
| 4,487,757 | 12/1984 | Kiozpeopeou .............................. 424/49 |
| 4,568,534 | 2/1986 | Stier et al. ................................. 424/7.1 |
| 5,154,917 | 10/1992 | Ibrahim et al. ............................ 424/7.1 |
| 5,296,215 | 3/1994 | Burke et al. ............................... 424/49 |
| 5,372,803 | 12/1994 | Williams et al. ........................... 424/53 |
| 5,525,330 | 6/1996 | Gaffar et al. ............................... 424/52 |
| 5,571,501 | 11/1996 | Toy ............................................ 424/49 |
| 5,646,178 | 7/1997 | Walker et al. ............................ 514/456 |
| 5,840,322 | 11/1998 | Weiss et al. .............................. 424/405 |

FOREIGN PATENT DOCUMENTS

WO 95/02392   1/1995   WIPO .

*Primary Examiner*—Sandra E. Saucier
*Assistant Examiner*—Vera Afremova
*Attorney, Agent, or Firm*—Angela Marie Stone; Mary Catherine Hentz; Douglas C. Mohl

[57] ABSTRACT

The present invention relates to an oral formulation contained in physically separated compartments of a suitable dispenser, comprising a first oral composition comprising from about 0.5% to about 50% of an alkali metal bicarbonate salt and from about 50% to about 99.5% of one or more aqueous carriers; and a second oral composition comprising a safe and effective amount of a plant species of the Ericaceae family or its extract and from about 40% to about 99.9% of one or more aqueous carriers.

15 Claims, No Drawings

… …

DUAL PHASE ORAL COMPOSITIONS COMPRISING A PLANT EXTRACT FROM THE ERICACEAE FAMILY

BACKGROUND OF THE INVENTION

The present invention relates to two phase oral formulations which contain ingredients when upon contact with each other neutralize and produce an effervescent effect. This invention comprises a basic phase which comprises an alkali metal bicarbonate salt and an acidic phase which comprises a plant species or extract of the Ericaceae family.

Oral care products consisting of separated first and second compositions which when brought together effervescence are already known in the art. U.S. Pat. No. 3,729,553, issued Apr. 24, 1973, to Gold et al., discloses an effervescing mouthwash composition. Effervescing toothpastes are disclosed in U.S. Pat. No. 4,487,757, issued Dec. 11, 1984, to Kiozpeoplou, and in WO 95/02392, published Jan. 26, 1995. Additionally, an observation that cranberry juice and other beverages could inhibit enzymes from plaque is noted in S. Kasket et al, "In-vitro Inhibition of Glucosyltransferase From Plaque Bacterium Streptococcus Mutans by Common Beverage and Food Extracts", Arch Oral Biology, Vol 30, No. 11/12, pp 821–826, 1985. Oral care products comprising a member of the Ericaceae family have been described in U.S. patent application Ser. No. 08/401,316, filed Mar. 9, 1995, incorporated herein by reference in its entirety.

The present inventors have discovered that an improved effervescent oral composition can be developed comprising a plant species or extract from the Ericaceae family. By adding the plant species or extract to the oral composition, an oral composition with improved antiplaque, antigingivitis, antiperiodontitis, anticaries, and anticalculus benefits is developed. Aesthetic benefits are also obtained through the use of plant extracts of the Ericaceae family including improved oral stimulation from the effervescence, improved cleaning impression from the astringent mouthfeel, and improved foaming and toothpaste dispersion from the carbon dioxide generation. The composition comprising the plant species or extract from the Ericaceae family will preferably be a red gel that is dispensed with a white paste to form the two phase oral formulation. The foam produced from this formulation is a light red color initially, but when neutralization occurs the foam turns a grayish white color. This color change may be used as a signal to consumers that their oral cleaning is complete.

Therefore, it is an object of the present invention to provide stable oral formulations comprising two oral compositions which are contained in physically separated compartments. The first oral composition comprises an alkali metal bicarbonate salt while the second oral composition comprises a plant species of the Ericaceae family or its extract. It is also an object of the present invention to provide a first oral composition comprising sodium bicarbonate, a soluble fluoride source, a tartar control agent, calcium peroxide, an abrasive polishing material, and one or more aqueous carriers and a second oral composition comprising a cranberry extract, an acidic compound, and one or more aqueous carriers. It is also an object of the present invention to provide oral formulations with antiplaque, anticalculus, and anticaries effects.

These and other objects of the present invention will become readily apparent from the detailed description which follows.

All percentages and ratios used herein are by weight of the specific oral composition and not of the overall oral formulation that is delivered, unless otherwise specified. All measurements are made at 25° C., unless otherwise specified.

SUMMARY OF THE INVENTION

The present invention relates to an oral formulation contained in physically separated compartments of a suitable dispenser, comprising a first oral composition comprising from about 0.5% to about 50% of an alkali metal bicarbonate salt and from about 50% to about 99.5% of one or more aqueous carriers; and a second oral composition comprising a safe and effective amount of a plant species of the Ericaceae family or its extract and from about 40% to about 99.9% of one or more aqueous carriers.

DETAILED DESCRIPTION OF THE INVENTION

The oral formulation of the present invention may be in the form of a toothpaste, dentifrice or mouthrinse. The term "oral formulation" as used herein means the combination of the two or more dentifrice or mouthrinse compositions. The oral formulation is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. Each dentifrice composition will be contained in a physically separated compartment of a dispenser and dispensed side-by-side.

The term "dispenser", as used herein, means any pump, tube, bottle, or container suitable for dispensing a dentifrice or mouthrinse.

By "safe and effective amount" as used herein means a sufficient amount of material to provide the desired benefit while still being safe to the hard and soft tissues of the oral cavity.

The term "aqueous carrier" as used herein means any safe and effective materials for use in the compositions of the present invention. Such materials include abrasive polishing materials, buffering agents, calcium peroxide, thickening materials, humectants, water, surfactants, titanium dioxide, flavor system, coolants, sweetening agents, xylitol, coloring agents, antimicrobial agents, and mixtures thereof.

The present compositions comprise essential components, as well as optional components. The essential and optional components of the compositions of the present invention are described in the following paragraphs.

Alkali Metal Bicarbonate Salt

The first oral composition of the present invention will include an alkali metal bicarbonate salt. Sodium bicarbonate, also known as baking soda, is the preferred alkali metal bicarbonate salt. The present composition will contain from about 0.5% to about 50%, preferably from about 2% to about 20%, more preferably from about 3% to about 15%, and most preferably from about 5% to about 12% of an alkali metal bicarbonate salt, by weight of the oral composition.

Plants or extracts of the Family Ericaceae

The second oral composition of the present invention will include a plant species or its extract from the Ericaceae family. The Ericaceae (heath) family, consisting of about 110 genera and 4,000 species, is by far the most important family of the Ericales order, encompassing a wide variety of fruit producing shrubbery and evergreen plants. Genera falling under Ericaceae family include Vaccinium, Arctostaphylos, Gaultheria, and Gaylussacia. The Arctostaphylos genus includes such species as the checkerberry and bearberry (*Uva ursi*). Other edible fruits such as the creeping snowberry or moxie plum fall under the genus Gaultheria. Huckleberries are a well known species of the genus Gaylussacia. The Vaccinium genus, best known for its fruits, contain some of the most common of berries, including the blueberry (e.g., *V. australe*), cranberry (e.g., *V. macrocarpon*) and bilberry (e.g., *V. myrtillus*). The term "berry (ies)," as used herein, means berries, drupes, plums and the like.

Plants or extracts useful in the compositions of the present invention come from a wide range of Ericaceae genera including, but not limited to, Vaccinium, Arctostaphylos, Gaultheria, and Gaylussacia. Preferred species include, *V. australe, V. corymbosum, V. occidentale, V. ovatum, V. myrtillus, V. parvifolium, V. uliginosum, V. macrocarpon, V. oxycoccus, V. erythrocarpum, V. vitis-idaea. V. australe, V. macrocarpon.* Vaccinium species most preferred for use in the present invention include *V. australe, V. macrocarpon,* and *V. myrtillus.* Mixtures of Ericaceae plants and/or extracts may also be used.

Agents which may provide activity from berries are the pigments found in the skins of the berries. Cranberry pigments fall into two main groups. The plastid pigments are associated with protoplasmic structure and include water-insoluble chlorophylls, carotene, and xanthophyll. The sap soluble pigments include the anthocyanins and anthoxanthins. These agents providing the antiplaque, antitartar, and anticaries efficacy will be found in the plants and their extracts.

Preferred forms of the extracts from the family Ericaceae include cranberry juice concentrates, cranberry juice powder, and other forms of cranberry which can serve as a proton donor. The most preferred form would include sugar-free extracts. Suitable forms of cranberry extract include the 50° Brix juice concentrate supplied by International Flavors and Fragrances and the 90MX cranberry powder from Ocean Spray. A safe and effective amount of a plant species of the Ericaceae family or its extract will be present in the second oral composition. A safe and effective amount means a sufficient amount of material to provide antiplaque, anticalculus, and anticaries effects, while still being safe to the hard and soft tissues of the oral cavity. Typically, a plant species of the Ericaceae family or its extract will be present in the second oral composition at a level of from about 0.1% to about 60%, preferably from about 1% to about 30%, and more preferably from about 3% to about 10%, by weight of the oral composition.

Fluoride Ion Source

The first and/or second oral compositions of the present invention may incorporate a soluble fluoride ion source capable of providing free fluoride ions. Although the plant or extract from the family Ericaceae may provide anticaries activity, the present invention may additionally include a fluoride ion source for additional anticaries activity. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety. If the fluoride ion source is present in the second dentifrice composition and an abrasive polishing material is also present, it is preferred that the composition additionally comprise a material like mineral oil. The fluoride ion source should be capable of providing from about 50 ppm to about 3500 ppm, and preferably from about 500 ppm to about 3000 ppm of free fluoride ions.

Tartar Control Agents

Although the plant or extract from the family Ericaceae may provide antitartar activity, the present invention may additionally include a specific agent for controlling tartar. The tartar control agent may be present in the first or second oral compositions or both compositions. The tartar control agent may be any materials known to be effective in reducing calcium phosphate mineral deposition related to calculus formation. The preferred tartar control agent is selected from the group consisting of a polyphosphate source, tripolyphosphate source, a pyrophosphate salt, and mixtures thereof.

The pyrophosphate salts useful in the present compositions include the di and tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 0.5% free pyrophosphate ions. Compositions comprising pyrophosphate typically containing from about 1% to about 15%, preferably from about 2% to about 10%, and most preferably from about 2% to about 8%, by weight of the composition. The pyrophosphate salts are described in U.S. Pat. No. 4,515,772, issued May 7, 1985, and U.S. Pat. No. 4,885,155, issued Dec. 5, 1989, both to Parran et al., incorporated herein by reference in their entirety, as well as the references disclosed therein.

The present invention may include a polyphosphate source. A polyphosphate is generally understood to consist of two or more phosphate molecules arranged primarily in a linear configuration, although some cyclic derivatives may be present. The inorganic polyphosphate salts desired include sodium tripolyphosphate, tetrapolyphosphate, and hexametaphosphate, among others. Polyphosphates larger than tetrapolyphosphate usually occur as amorphous glassy materials. Preferred are polyphosphates manufactured by FMC Corporation which are commercially known as Sodaphos (n≈6), Hexaphos (n≈13), and Glass H (n≈21). The polyphosphate source will typically comprise from about 0.5% to about 20%, preferably from about 4% to about 15%, more preferably from about 6% to about 10%, and most preferably from about 7% to about 9%, by weight of the oral composition.

The phosphate sources are described in more detail in Kirk & Othmer, *Encyclopedia of Chemical Technology,* Fourth Edition, Volume 18, Wiley-Interscience Publishers (1996), pages 685–707, incorporated herein by reference in its entirety, including all references incorporated into Kirk & Othmer. Optional agents to be used in place of or in combination with the polyphosphate or pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

Aqueous Carriers

In preparing the present compositions, it is desirable to add one or more aqueous carriers to the oral compositions. Such materials are well known in the art and are readily chosen by one skilled in the art based on the physical and aesthetic properties desired for the compositions being prepared. Aqueous carriers typically comprise from about 10% to about 99.9%, preferably from about 50% to about 98%, and more preferably from about 60% to about 96%, by weight of the oral composition.

Abrasive Polishing Materials

An abrasive polishing material may also be included in one or both of the dentifrice compositions. The abrasive polishing material contemplated for use in the compositions of the present invention can be any material which does not excessively abrade dentin. Typical abrasive polishing materials include silicas including gels and precipitates; aluminas; phosphates including orthophosphates, polymetaphosphates, and insoluble pyrophosphates; and mixtures thereof. Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, and in U.S. Pat. No. 5,589,160, issued Dec. 31, 1996, and U.S. Pat. No. 5,603,920, issued Feb. 18, 1997, both to Rice, incorporated herein by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the dentifrice compositions. The peroxide source is selected from the group consisting of hydrogen peroxide, calcium peroxide, urea peroxide, and mixtures thereof. The preferred peroxide source for the first oral composition is calcium peroxide and the preferred peroxide source for the second oral composition is hydrogen peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the oral composition.

Buffering Agent

The oral compositions may each contain a buffering agent. Buffering agents, as used herein, refer to agents that can be used to adjust the pH of the compositions. In the first oral composition, the pH is adjusted to a range of from about pH 8.0 to about pH 10.5. Preferably the pH is from about pH 8.0 to about pH 9.5 and more preferably from pH 8.2 to about pH 9.0. The buffering agents suitable include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, and pyrophosphate salts.

In addition to the plant or extract from the Ericaceae family, an additional acidic compound can be added to further lower the pH. In the second oral composition, the pH is adjusted to a range of from about pH 1.5 to about pH 6.5. Preferably the pH is from about pH 2.0 to about pH 6.0 and more preferably from about pH 2.5 to about pH 5.5. Suitable acidic compounds used as buffering agents for the second oral composition include carboxylic acids, phosphoric acids, alpha-hydroxy acids, sulfonic acids, and mixtures thereof. Specific acids include citric acid, malic acid, alginic acid, succinic acid, lactic acid, tartaric acid, glycolic acid, adipic acid, potassium bitartrate acid, acid sodium citrate, phosphoric acid, boric acid, and acid phosphate and pyrophosphate salts. A blend of acids are preferred. Phosphoric acid, citric acid, and malic acid are preferred. Acid anhydrides and acid salts of the above acids may also be used. Suitable salts include mono or disodium salts of citric acid, mono sodium salts of malic acid, and mixtures thereof. Buffering agents are used at a level of from about 0.1% to about 30%, preferably from about 1% to about 10%, and more preferably from about 1.5% to about 3%, by weight of the oral composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the oral composition.

Another optional component of the oral compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, polyoxyethylene, and other edible polyhydric alcohols. The polyethylene glycol or polyoxyethylene may have a molecular weight of from about 200 to about 7000. The humectant generally comprises from about 0% to 70%, and preferably from about 15% to 55%, by weight of the oral composition.

Water employed in the preparation of commercially suitable oral compositions should preferably be of low ion content and free of organic impurities. In the first or second oral compositions, water will generally comprise from about 5% to about 70%, and preferably from about 10% to about 50%, by weight of the composition herein. Alternatively, the dentifrice composition may comprise a lower level of water, generally from about 5% to about 20%, preferably from about 7% to about 14%, and more preferably from about 7% to about 12%, by weight of the dentifrice composition. The lower level of water is preferred in compositions comprising polyphosphates. The amounts of water include the free water which is added plus that which is introduced with other materials, such as with sorbitol, silica, surfactant solutions, and/or color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate). Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Many of these suitable surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, cranberry, propenyl guaethol, cinnamon, vanillin, ethyl vanillin, heliotropine, 4-cis-heptenal, diacetyl, methyl-para-tert-butyl phenyl acetate, and mixtures thereof. The second oral composition comprising a plant or extract from the Ericaceae family may also contain an additional artificial or natural flavor. The flavor may be cranberry, which will enhance the overall cranberry flavor. Alternatively, the flavor may be a more typical oral care flavor, such as a mint flavor. Preferably, the first oral composition will comprise a mint flavor and the second oral composition will comprise a cranberry flavor. A flavor system is generally used in the compositions at levels of from about 0.001% to about 5%, by weight of the composition.

Coolants may also be part of the flavor system or added separately to the composition. Preferred coolants in the present compositions are the paramenthan carboxyamide agents such as N-ethyl-p-menthan-3-carboxamide (known commercially as "WS-3"), menthol, 3-1-menthoxypropane-1,2-diol ("TK-10"), menthone glycerol acetal ("MGA"), menthyl lactate, and mixtures thereof. A coolant is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an anti-bacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition.

Alternatively, if xylitol is used as a sweetener, it may be present at a lower level, such as from about 0.005% to about 5%, by weight of the oral composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents and water soluble antimicrobials, such as quaternary ammonium salts and bis-biquanide salts, among others. Triclosan monophosphate is an additional water soluble antimicrobial agent. Other compounds are bis[4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 1.5%, by weight of the oral composition.

The oral formulation may be a dentifrice or mouthrinse. If the oral formulation is a dentifrice, the first and second dentifrice compositions will be physically separated in a dentifrice dispenser. The dentifrice compositions may be a paste, gel, or any configuration or combination thereof. It is preferred that the first dentifrice composition be a white paste and the second dentifrice composition be a red gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

Alternatively, the oral formulation may be a mouthrinse. Again, the first and second mouthrinse compositions will be physically separated until dispensed. Dual compartment packages suitable for this purpose are described in U.S. Pat. No. 3,729,553, issued Apr. 24, 1973, U.S. Pat. No. 5,252,312, issued Oct. 12, 1993, U.S. Pat. No. 5,289,950, issued Mar. 1, 1994, and U.S. Pat. No. 5,392,947, issued Feb. 28, 1995, all incorporated herein in their entirety.

Once the two compositions are intermixed, the oral formulation will produce an effervescent effect. The neutralized pH of this intermixed composition will be from about pH 6.0 to about pH 7.5 and preferably from about pH 6.5 to about pH 7.0. In a preferred formulation, the first component is a white paste and the second component is a red gel. The foam in the mouth starts out as a light red foam, but when the neutralization occurs and the color of foam changes to a grayish color.

The present compositions can be in the form of a mouth rinse or liquid dentifrice where conventional mouth rinse components comprise the aqueous carriers of the present invention. Mouth rinses and liquid dentifrices generally comprise from about 20:1 to about 2:1 of a water ethyl alcohol or alcohol free solution, and preferably other ingredients such as flavors, sweeteners, and humectants as those mentioned above. The humectants, such as glycerin and sorbitol, give a moist feel to the mouth. In addition to the alkali metal bicarbonate salt and the plant or extract from the Ericaceae family, generally on a weight basis, the mouth rinses and liquid dentifrices of the present invention comprise from about 0% to about 60% ethyl alcohol, from about 0% to about 20% humectant, from about 0% to about 0.5% sweetening agent, from about 0% to about 0.3% of a flavoring system, and the balance water.

Method of Treatment

The method of treatment herein comprises contacting the dental enamel surfaces in the mouth with the oral compositions according to the present invention.

Examples & Method of Manufacturing

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| First Dentifrice Composition | | Second Dentifrice Composition | |
| --- | --- | --- | --- |
| Ingredient | Wt. % | Ingredient | Wt. % |
| Carboxymethylcellulose | 0.85 | Color | 0.30 |
| Water | 3.00 | Water | 6.00 |
| Flavor | 1.00 | Flavor | 0.50 |
| Glycerin | 10.00 | Glycerin | 28.00 |
| Polyethylene Glycol | 1.00 | Poloxamer 407 | 18.00 |
| Sorbitol[b] | 37.30 | Sodium Saccharin | 0.50 |
| Sodium Alkyl Sulfate[a] | 10.00 | Cranberry Concentrate[c] | 47.00 |
| Silica | 15.00 | | |
| Sodium Carbonate | 1.00 | | |
| Sodium Saccharin | 0.50 | | |
| Sodium Bicarbonate | 20.00 | | |
| Titanium Dioxide | 0.35 | | |

[a] 27.9% solution
[b] 70% solution
[c] 50° Brix

Example I is prepared as follows. The first dentifrice composition is prepared by adding the water and saccharin to a mixing vessel. Disperse the carboxymethyl cellulose in the glycerin and sorbitol. Add this mixture of dispersed thickening agents to the mixing vessel and mix well. Add the flavor, polyethylene glycol, titanium dioxide, and sodium alkyl sulfate to the mixture and mix well. Next add the sodium carbonate and the silica. After mixing, add the sodium bicarbonate. Continue stirring the mixture until homogeneous.

The second dentifrice composition is prepared as follows. Add the water, saccharin, color, and cranberry to the mixing vessel. Add the glycerin and Poloxamer and mix until the Poloxamer melts. Finally, add the flavor and continue stirring the mixture until homogeneous.

EXAMPLE II

| First Dentifrice Composition | | Second Dentifrice Composition | |
| --- | --- | --- | --- |
| Ingredient | Wt. % | Ingredient | Wt. % |
| Carboxymethylcellulose | 0.40 | Water | 31.74 |
| Water | 5.00 | Poloxamer | 10.00 |
| Flavor | 1.00 | Cranberry Concentrate[c] | 6.50 |
| Glycerin | 33.40 | Phosphoric Acid | 0.40 |
| Poloxamer 407 | 3.00 | Silica | 20.00 |
| Propylene Glycol | 8.50 | Sodium Saccharin | 0.30 |
| Sodium Alkyl Sulfate[a] | 4.00 | Flavor | 0.50 |
| Silica | 20.50 | Glycerin | 9.00 |
| Sodium Carbonate | 2.00 | Carboxymethylcellulose | 0.30 |
| Sodium Saccharin | 0.40 | Xanthan Gum | 0.20 |
| Sodium Bicarbonate | 12.00 | Color | 0.06 |
| Titanium Dioxide | 1.00 | Mineral Oil | 1.00 |
| Xanthan Gum | 0.20 | Sorbitol[b] | 20.00 |
| Glass H Polyphosphate | 4.00 | | |
| Polyethylene Glycol | 3.00 | | |
| Coolant | 0.60 | | |
| Polyoxyethylene | 1.00 | | |

[a] 27.9% solution
[b] 70% solution
[c] 50° Brix

EXAMPLE III

| First Dentifrice Composition | | Second Dentifrice Composition | |
|---|---|---|---|
| Ingredient | Wt. % | Ingredient | Wt. % |
| Carboxymethylcellulose | 0.40 | Water | 23.15 |
| Water | 5.00 | Poloxamer | 20.00 |
| Flavor | 1.00 | Cranberry Concentrate[c] | 20.00 |
| Glycerin | 34.40 | Phosphoric Acid | 0.20 |
| Poloxamer 407 | 3.00 | Silica | 10.00 |
| Propylene Glycol | 8.50 | Sodium Saccharin | 0.40 |
| Sodium Alkyl Sulfate[a] | 4.00 | Flavor | 0.25 |
| Silica | 20.50 | Glycerin | 25.00 |
| Sodium Carbonate | 2.00 | Color | 0.02 |
| Sodium Saccharin | 0.40 | Coolant | 0.50 |
| Sodium Bicarbonate | 12.00 | Sodium Fluoride | 0.48 |
| Titanium Dioxide | 1.00 | | |
| Xanthan Gum | 0.20 | | |
| Glass H Polyphosphate | 4.00 | | |
| Polyethylene Glycol | 3.00 | | |
| Coolant | 0.60 | | |

[a]27.9% solution
[c]50° Brix

Examples II and III are made as follows. The first dentifrice compositions are prepared by adding the water and saccharin to a mixing vessel. Disperse the thickening agents, carboxymethyl cellulose and xanthan gum, in the glycerin. Add this mixture of dispersed thickening agents in glycerin to the mixing vessel and mix well. Add the flavor, coolant, Poloxamer, polyoxyethylene (if used), polyethylene glycol, propylene glycol, titanium dioxide, and sodium alkyl sulfate to the mixture and mix well. Next add the sodium carbonate and the silica. After mixing, add the sodium bicarbonate. Finally, add the polyphosphate. Continue stirring the mixture until homogeneous.

The second dentifrice compositions for Example II is prepared as follows. Add the water, saccharin, cranberry, sorbitol, mineral oil, color, and acid to the mixing vessel. Disperse the thickening agents, carboxymethyl cellulose and xanthan gum, in the glycerin. Add this mixture of dispersed thickening agents in glycerin to the mixing vessel and mix well. Add the Poloxamer and heat until the Poloxamer melts. Add the silica into the mixture and mix for at least 10 minutes. Finally, add the flavor. Continue stirring the mixture until homogeneous.

The second dentifrice compositions for Example III is prepared as follows. Add the water, saccharin, fluoride, cranberry, color, and acid to the mixing vessel. Add the Poloxamer and glycerin and mix well. Add the silica into the mixture and mix for at least 10 minutes. Finally, dissolve the coolant in the flavor and add to the mixture. Continue stirring the mixture until homogeneous.

EXAMPLE IV

| First Dentifrice Composition | | Second Dentifrice Composition | |
|---|---|---|---|
| Ingredient | Wt. % | Ingredient | Wt. % |
| Carboxymethylcellulose | 0.80 | Poloxamer | 15.00 |
| Water | 10.00 | Cranberry Concentrate[c] | 55.00 |
| Flavor | 1.60 | Silica | 5.00 |
| Glycerin | 8.00 | Sodium Saccharin | 0.40 |
| Polyethylene Glycol | 3.00 | Glycerin | 20.05 |
| Propylene Glycol | 8.50 | Carboxymethylcellulose | 0.20 |
| Sodium Alkyl Sulfate[a] | 4.00 | Xanthan Gum | 0.15 |
| Silica | 20.00 | Polyethylene Glycol | 3.00 |
| Sodium Carbonate | 1.90 | Hydrogen Peroxide | 1.20 |
| Sodium Saccharin | 0.40 | | |
| Sodium Bicarbonate | 10.00 | | |
| Titanium Dioxide | 1.00 | | |
| Sorbitol[b] | 30.40 | | |
| Sodium Fluoride | 0.40 | | |

[a]27.9% solution
[b]70% solution
[c]50° Brix

Example IV is prepared as follows. The first dentifrice composition is prepared by adding the water, saccharin, and fluoride to a mixing vessel. Disperse the carboxymethyl cellulose in the glycerin and sorbitol. Add this mixture of dispersed thickening agents to the mixing vessel and mix well. Add the flavor, polyethylene glycol, propylene glycol, titanium dioxide, and sodium alkyl sulfate to the mixture and mix well. Next add the sodium carbonate and the silica. After mixing, add the sodium bicarbonate. Continue stirring the mixture until homogeneous.

The second dentifrice composition is prepared as follows. Add the cranberry and saccharin to the mixing vessel. Disperse the carboxymethylcellulose and xanthan gum in the glycerin and add to the mixture. Add the Poloxamer and polyethylene glycol and mix until the Poloxamer melts. Add the hydrogen peroxide. Finally, add the silica and continue stirring the mixture until homogeneous.

EXAMPLE V

| First Dentifrice Composition | | Second Dentifrice Composition | |
|---|---|---|---|
| Ingredient | Wt. % | Ingredient | Wt. % |
| Water | 15.73 | Water | 4.50 |
| Poloxamer | 4.00 | Poloxamer | 11.75 |
| Carboxymethylcellulose | 0.40 | Cranberry Concentrate[c] | 38.50 |
| Xanthan Gum | 0.07 | Phosphoric Acid | 0.14 |
| Flavor | 1.00 | Sodium Saccharin | 0.28 |
| Silica | 15.00 | Flavor | 0.30 |
| Propylene Glycol | 10.00 | Glycerin | 25.00 |
| Sodium Saccharin | 0.40 | Carboxymethylcellulose | 0.20 |
| Sodium Alkyl Sulfate[a] | 4.00 | Xanthan Gum | 0.10 |
| Titanium Dioxide | 1.00 | Color | 0.03 |
| Glycerin | 34.40 | Mineral Oil | 1.00 |
| Sodium Bicarbonate | 12.00 | Coolant | 0.20 |
| Sodium Carbonate | 2.00 | Sorbitol[b] | 18.00 |

[a]27.9% solution
[b]70% solution
[c]50° Brix

EXAMPLE VI

| First Dentifrice Composition | | Second Dentifrice Composition | |
|---|---|---|---|
| Ingredient | Wt.% | Ingredient | Wt. % |
| Water | 15.73 | Water | 26.14 |
| Poloxamer | 4.00 | Poloxamer | 3.00 |
| Carboxymethylcellulose | 0.40 | Cranberry Concentrate[c] | 1.35 |
| Xanthan Gum | 0.07 | Phosphoric Acid | 0.55 |
| Flavor | 1.00 | Sodium Saccharin | 0.40 |
| Silica | 15.00 | Flavor | 0.55 |
| Propylene Glycol | 10.00 | Glycerin | 20.00 |

-continued

| First Dentifrice Composition | | Second Dentifrice Composition | |
|---|---|---|---|
| Ingredient | Wt.% | Ingredient | Wt. % |
| Sodium Saccharin | 0.40 | Carboxymethylcellulose | 0.40 |
| Sodium Alkyl Sulfate(a) | 4.00 | Xanthan Gum | 0.20 |
| Titanium Dioxide | 1.00 | Color | 0.08 |
| Glycerin | 34.40 | Mineral Oil | 1.00 |
| Sodium Bicarbonate | 12.00 | Coolant | 0.65 |
| Sodium Carbonate | 2.00 | Sorbitol(b) | 20.00 |
| | | Silica | 20.00 |
| | | Titanium Dioxide | 1.00 |
| | | Polyethylene Glycol | 3.00 |
| | | Hydrogen Peroxide | 1.20 |
| | | Sodium Fluoride | 0.48 |

(a)27.9% solution
(b)70% solution
(c)50° Brix

Examples V and VI are prepared as follows. The first dentifrice composition is prepared by adding the water and saccharin to a mixing vessel. Disperse the carboxymethyl cellulose and xanthan gum in the glycerin. Add this mixture of dispersed thickening agents to the mixing vessel and mix well. Add the Poloxamer, flavor, propylene glycol, titanium dioxide, and sodium alkyl sulfate to the mixture and mix until the Poloxamer melts. Next add the sodium carbonate and the silica. After mixing, add the sodium bicarbonate. Continue stirring the mixture until homogeneous.

The second dentifrice composition for Example V is prepared as follows. Add the water, saccharin, color, phosphoric acid, and cranberry to the mixing vessel. Disperse the carboxymethyl cellulose and xanthan gum in the glycerin and sorbitol. Add this mixture to the mixing vessel. Add the Poloxamer, mineral oil, flavor, and coolants and continue stirring the mixture until homogeneous.

The second dentifrice composition for Example VI is prepared as follows. Add the water, saccharin, fluoride, phosphoric acid, color, and cranberry to the mixing vessel. Disperse the carboxymethyl cellulose and xanthan gum in the glycerin and sorbitol. Add this mixture to the mixing vessel. Next, add the silica. Add the Poloxamer, titanium dioxide, and polyethylene glycol and mix until the Poloxamer melts. Add the mineral oil, flavor, and coolants. Finally, add the hydrogen peroxide. Continue stirring the mixture until homogeneous.

EXAMPLE VII

| First Mouthrinse Composition | | Second Mouthrinse Composition | |
|---|---|---|---|
| Ingredient | Wt. % | Ingredient | Wt. % |
| Glycerin | 9.69 | Glycerin | 10.80 |
| Water | 65.00 | Water | 60.00 |
| Saccharin | 0.06 | Saccharin | 0.06 |
| Flavor | 0.20 | Flavor | 0.10 |
| Propylene Glycol | 5.00 | Propylene Glycol | 5.00 |
| Sodium Carbonate | 0.05 | Color | 0.04 |
| Sodium Bicarbonate | 5.00 | Phosphoric Acid | 4.00 |
| Ethanol | 15.00 | Ethanol | 15.00 |
| | | Cranberry Concentrate(c) | 5.00 |

(c)50° Brix

Example VII is prepared as follows. Combine the water and saccharin in a mixing vessel. For the second composition, add the cranberry and color. Next, add the glycerin and propylene glycol. Add the flavor system and ethanol. Finally, add the sodium carbonate and bicarbonate for the first composition or the phosphoric acid for the second composition. Continue mixing each composition until homogeneous.

EXAMPLE VIII

| First Mouthrinse Composition | | Second Mouthrinse Composition | |
|---|---|---|---|
| Ingredient | Wt.% | Ingredient | Wt. % |
| Glycerin | 9.57 | Glycerin | 10.80 |
| Water | 65.09 | Water | 58.02 |
| Sodium Saccharin | 0.07 | Sodium Saccharin | 0.07 |
| Propylene Glycol | 5.00 | Propylene Glycol | 5.00 |
| Ethanol | 15.00 | Ethanol | 15.00 |
| Flavor | 0.10 | Flavor | 0.10 |
| Sodium Bicarbonate | 5.00 | Phosphoric Acid | 1.00 |
| Sodium Carbonate | 0.05 | Color | 0.01 |
| Cetyl Pyridinium Chloride | 0.11 | Cranberry Concentrate(c) | 10.00 |
| Domiphen Bromide | 0.01 | | |

(c)50° Brix

Example VIII is prepared as follows. Combine the water and saccharin in a mixing vessel. For the second composition, add the cranberry, acid, and color. Next, add the glycerin and propylene glycol. Add the flavor system and ethanol. For the first composition, add the sodium carbonate and bicarbonate followed by the cetyl pyridinium chloride, and domiphen bromide. Continue mixing each composition until homogeneous.

What is claimed is:

1. An oral formulation contained in physically separated compartments of a dispenser, comprising:
   a. a first oral composition comprising:
      (i) from about 0.5% to about 50% of an alkali metal bicarbonate salt; and
      (ii) from about 50% to about 99.5% of one or more aqueous carriers;
      wherein the first oral composition is a white dentifrice paste and
   b. a second oral composition comprising:
      (i) from about 0.1% to about 60% of a plant species of the Ericaceae family or its extract; and
      (ii) from about 40% to about 99.9% of one or more aqueous carriers;
      wherein the second oral composition is a red dentifrice gel;
   wherein the red gel combines with the white paste during brushing and is neutralized to produce a grayish white foam.

2. The oral formulation according to claim 1 wherein the plant species or its extract is selected from the genus Vaccinium.

3. The oral formulation according to claim 2 wherein the plant species or its extract is cranberry.

4. The oral formulation according to claim 3 wherein the second oral composition further comprises an acidic compound selected from the group consisting of carboxylic acids, phosphoric acids, alpha-hydroxy acids, sulfonic acids, and mixtures thereof.

5. The oral formulation according to claim 4 wherein the alkali metal bicarbonate salt of the first oral composition is sodium bicarbonate.

6. The oral formulation according to claim 5 wherein the first oral composition further comprises a soluble fluoride source capable of providing from about 50 ppm to about 3500 ppm of free fluoride ions.

7. The oral formulation according to claim 6 wherein the soluble fluoride source of the first oral composition is sodium fluoride.

8. The oral formulation according to claim 7 wherein the first oral composition further comprises an effective amount of an additional tartar control agent selected from the group consisting of polyphosphates, pyrophosphate salts, and mixtures thereof.

9. The oral formulation according to claim 8 wherein the first oral composition, second oral composition, or both oral compositions further comprise a linear polymeric polycarboxylate and an effective amount of an additional antimicrobial agent selected from the group consisting of zinc salts, triclosan, chlorhexidine, cetyl pyridinium chloride, and mixtures thereof.

10. The oral formulation according to claim 9 wherein the first oral composition further comprises from about 0.01% to about 10% of a peroxide source.

11. The oral formulation according to claim 10 wherein the pH of the first oral composition is from about 8.0 to about 10.5 and the pH of the second oral composition is from about 1.5 to about 6.5.

12. The oral formulation according to claim 11 wherein the aqueous carriers of the first and second oral compositions are materials selected from the groups consisting of abrasive polishing materials, buffering agent, thickening materials, humectants, water, surfactants, titanium dioxide, flavor system, sweetening agents, xylitol, coloring agents, and mixtures thereof.

13. An oral formulation contained in physically separated compartments of a dispenser, comprising:
  a. a first dentifrice composition comprising:
    (i) from about 0.5% to about 50% of sodium bicarbonate;
    (ii) a soluble fluoride source capable of providing from about 50 ppm to about 3500 ppm of free fluoride ions;
    (iii) an effective amount of an additional tartar control agent
    (iv) from about 0.01% to about 10% of calcium peroxide;
    (v) from about 10% to about 70% of an abrasive polishing material; and
    (vi) from about 10% to about 85% of one or more aqueous carriers;
    wherein the first dentifrice composition is a white paste and
  b. a second dentifrice composition comprising:
    (i) from about 0.1% to about 60% of cranberry extract;
    (ii) from about 0.5% to about 20% of an acidic compound; and
    (ii) from about 80% to about 99% of one or more aqueous carriers;
    wherein the second dentifrice composition is a red gel;
  wherein the red gel combines with the white paste during brushing and is neutralized to produce a grayish white foam.

14. A method for reducing the incidence of calculus on dental enamel comprising contacting the enamel surfaces in the mouth with the oral formulation according to claim 7.

15. A method for reducing the incidence of calculus on dental enamel comprising contacting the enamel surfaces in the mouth with the oral formulation according to claim 13.

* * * * *